(12) United States Patent
Bramlet et al.

(10) Patent No.: US 6,488,684 B2
(45) Date of Patent: Dec. 3, 2002

(54) INTRAMEDULLARY NAIL

(76) Inventors: Dale G. Bramlet, 2044 Brightwaters Blvd. NE., St. Petersburg, FL (US) 33704; Patrick J. Cosgrove, 12200 4th St. E., Treasure Island, FL (US) 33706; John A. Sodeika, 11650 Harborside Cir., Largo, FL (US) 33773; Peter M. Sterghos, 5291 40th Ave., St. Petersburg, FL (US) 33709

( * ) Notice: Subject to any disclaimer, the term of this patent is extended or adjusted under 35 U.S.C. 154(b) by 30 days.

(21) Appl. No.: 09/841,939

(22) Filed: Apr. 25, 2001

(65) Prior Publication Data

US 2002/0161369 A1 Oct. 31, 2002

(51) Int. Cl.[7] .............................................. A61B 17/72
(52) U.S. Cl. .......................................... 606/62; 606/67
(58) Field of Search ....................... 606/60–68

(56) References Cited

U.S. PATENT DOCUMENTS

| | | | |
|---|---|---|---|
| 4,653,487 A | * | 3/1987 | Maale ................... 128/92 VQ |
| 4,862,883 A | | 9/1989 | Freeland |
| 5,810,820 A | | 9/1998 | Santori et al. |
| 5,849,004 A | * | 12/1998 | Bramlet ...................... 606/232 |
| 5,879,352 A | * | 3/1999 | Filoso et al. .................. 606/62 |
| 5,971,986 A | | 10/1999 | Santori et al. |
| 5,976,139 A | | 11/1999 | Bramlet |
| 6,077,264 A | | 6/2000 | Chemello |
| 6,126,661 A | | 10/2000 | Faccioli et al. |

FOREIGN PATENT DOCUMENTS

FR  2606269  *  5/1988  ................... 606/67

* cited by examiner

*Primary Examiner*—Nicholas D. Lucchesi
*Assistant Examiner*—Michael B. Priddy
(74) *Attorney, Agent, or Firm*—McHale & Slavin, P.A.

(57) ABSTRACT

An intramedullary nail system for reducing and fixing fractures in long bones includes an elongated intramedullary nail having radial portals about the circumference. Tang assemblies are slidably telescoped inside the nail with resilient tangs which are deployed through the portals to interlock the nail and the portions of the bone.

14 Claims, 5 Drawing Sheets

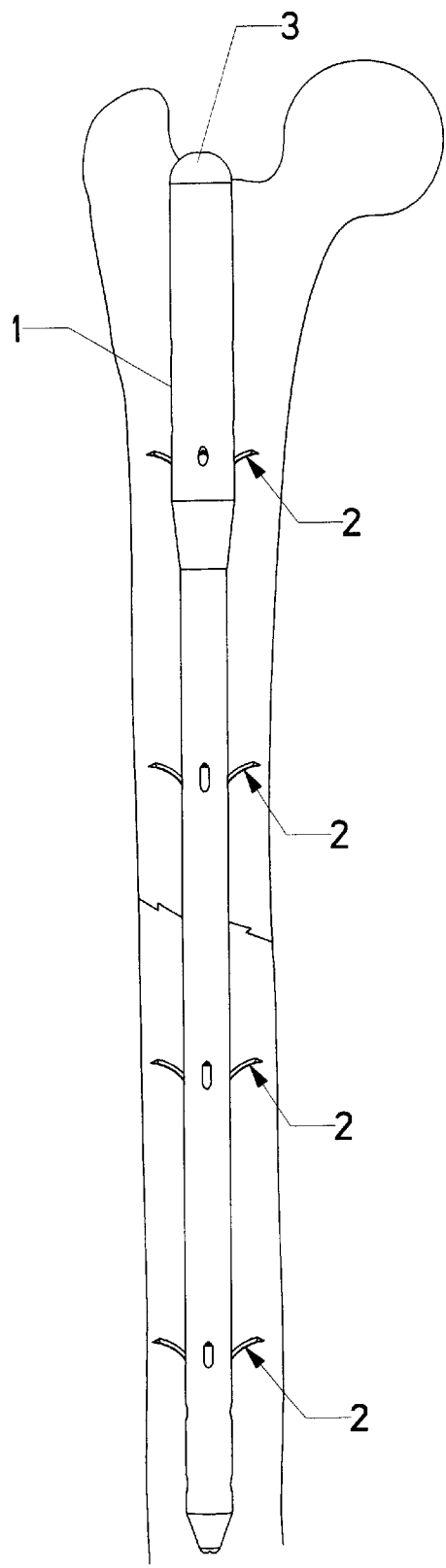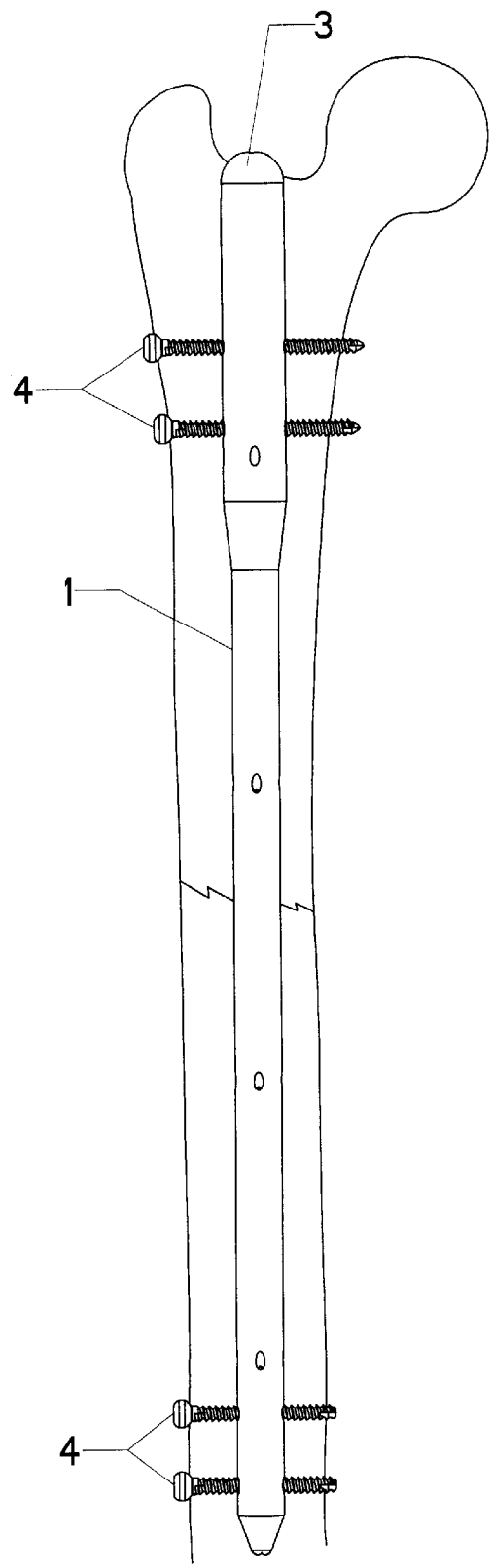
FIG. 1
FIG. 2

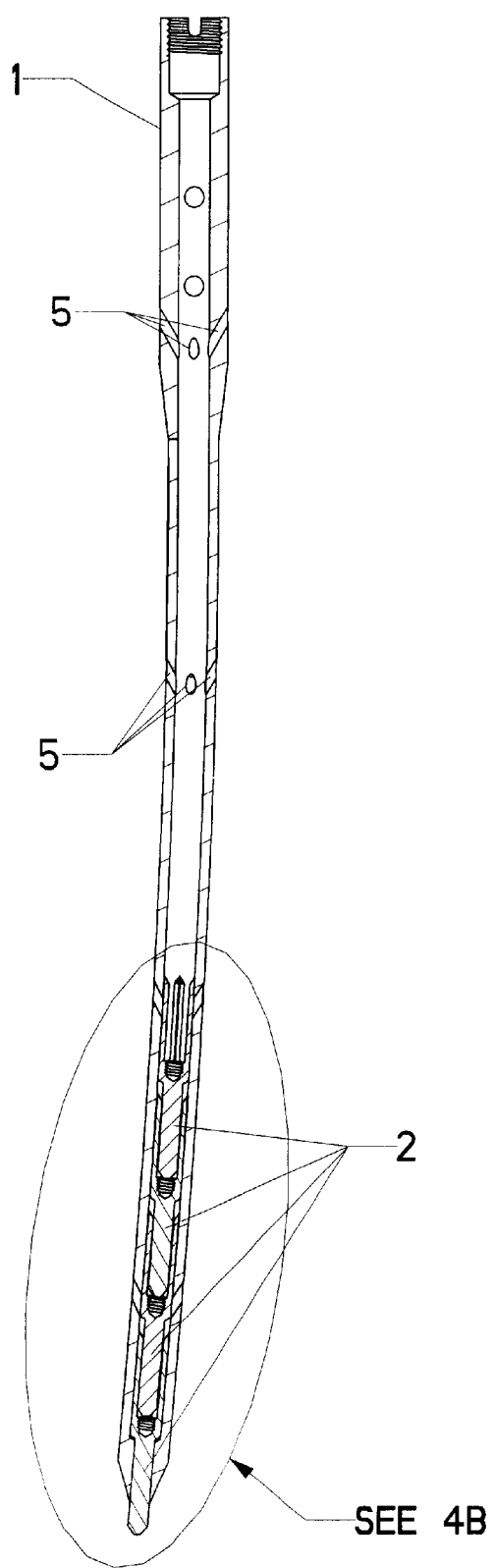
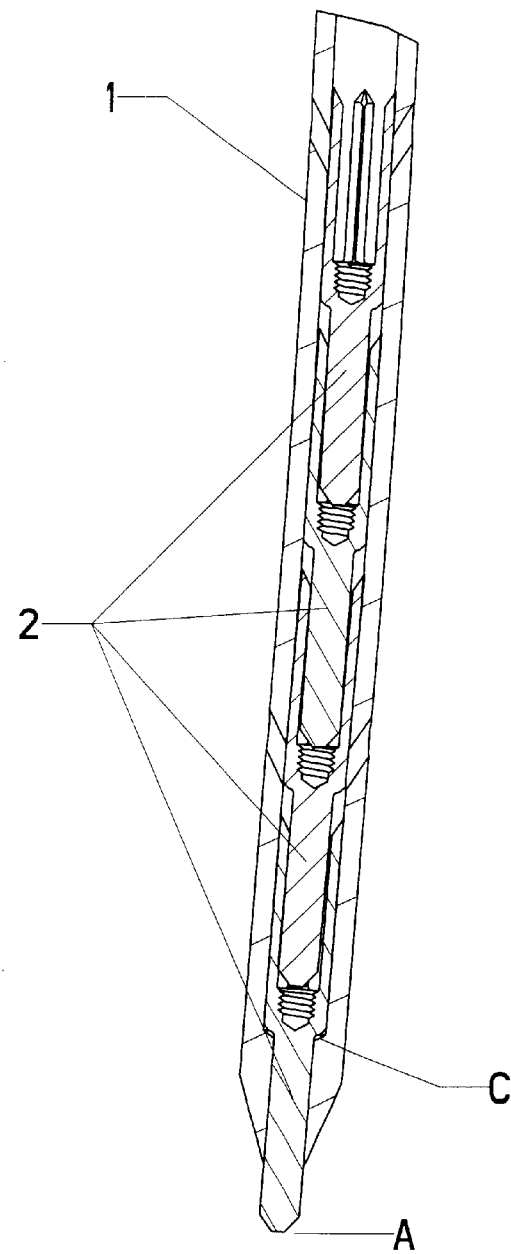
FIG. 4A
FIG. 4B

INTRAMEDULLARY NAIL

FIELD OF THE INVENTION

The present invention generally relates to an intramedullary nail system for reducing and fixing bone portions across a fracture therebetween providing a means of fixation through the use of tangs, screws or a combination of both.

BACKGROUND OF THE INVENTION

In its most basic construct bones are formed of a relatively soft, spongy cancellous material surrounded by a much harder cortex. The cancellous bone yields under relatively low loading, while the much more dense cortical bone supports much higher loading. There have been a number of techniques used historically for treatment of fractures of the femur, humerus or tibia (referred to as the long bones). In early parts of this century, patients were merely placed in bed-or in traction for prolonged periods, frequently resulting in deformity or death.

In the 1930s, the Smith-Peterson nail was introduced. This device was inserted into the intramedullary canal of the femur resulting in immediate fixation of hip fractures, early mobilization of the patient, and a lower morbidity and mortality. A number of nails have been introduced for intramedullary fracture fixation of long bones, including the Jewett Nail and Enders Nail.

Later intramedullary nails increased in diameter and surgeons/inventors began to experiment with cross section designs and radii of curvature along the nail's length. Since the femur curves slightly along its length, it was preferred that the nails have a similar long radius of curvature of, for example 50 inches. These nails were inserted down the entire length of the femoral canal to provide a basis for the construct. Fixation methods for certain types of fractures often required the nail to bear a portion of the patient's weight during the recovery period. Threaded wires, standard bone screws or cannulated bone screws were then inserted through or along side the nail and into the outer cortex to provide enough fixation and rotational stability to bear weight during recovery.

As these intramedullary nails became longer other problems occurred. In longer nails the distal tip of the nail tends to rotate out of plane which forces the surgeon to target the distal screw holes using fluoroscopy by a method commonly known as "free-handing". Under this technique the surgeon utilizes fluoroscopic images in search of perfectly circular screw holes. Once found a mark is made on the patient, an incision is made and a pathway cleared to the cortical bone. A dimple is placed on the lateral cortex to reduce "drill walking" and the hole is then drilled and a screw inserted. Adjustments to this procedure are quite common; even to those skilled in the art of free handing.

Numerous patents, both domestic and foreign, have been granted citing devices which reduce the complications associated with distal screw targeting. The methods of accomplishing this task are varied, but the results are the same: Very few of the ideas have been developed and marketed as useful products. The majority of surgeons still return to free handing because there is a perceived time savings. Therefore, external methods for distal screw targeting have not gained favor.

DESCRIPTION OF THE PRIOR ART

Newer devices and inventions explored additions to the nail to eliminate the need to locate the distal screw holes and improve the fixation. These newer devices are commonly classified as "expanding devices" and expand in size after placement to fill the intramedullary cavity. In the early 1980s, the Brooker-Wills Nail came on the scene and others soon followed. Freedland, U.S. Pat. Nos. 4,632,101, 4,862,883 and 4,721,103, Chemello, U.S. Pat. No. 6,077,264, and Davis, U.S. Pat. No. 5,057,103, describe methods of fixation which provide points which contact the internal cortical wall. In these patents a mechanism is actuated deploying arms or anchor blades through the cancellous bone to contact the inner cortical wall. These methods are complex and the arms are difficult to retract should the nail or lag screw assembly requires extraction. These arms do not deploy through the cortical bone.

Other expanding devices provide surface contact with the internal cortical wall resulting in a wedge effect. Kurth, U.S. Pat. No. 4,590,930, Raftopoulos, U.S. Pat. No. 4,453,539, and Aginski, U.S. Pat. No. 4,236,512, among others have described mechanisms which deploy or expand with a molly bolt concept. These methods are complex and the devices are difficult to retract should the nail require extraction. Neither do these devices deploy through the cortical bone.

Bolesky, U.S. Pat. No. 4,275,717, was the first to discuss engagement within the cortical wall. However, Bolesky's invention does not address controlled penetration into the wall and required permanent implantation of the actuation rod. In addition, Bolesky does not address the fundamental problem of the actuation rod's protrusion extramedullarly into the surrounding musculature.

In U.S. Pat. Nos. 5,976,139 and 6,183,474B1, Bramlet et al describe a surgical anchor which has deployable tangs. These tangs are simple in design, internally positioned, yet easily deployed into, and if desired through, cortical bone providing improved purchase for compression of a proximal femur fracture, especially in osteogenic bone. These tangs are just as easily retracted should the device require explantation.

SUMMARY OF THE INVENTION

The intramedullary nail system according to this invention is especially suitable for installation within the medullary canal of a fractured long bone, such as a femur, humerus, or tibia and subsequently interlocking the nail and bone thereby preventing axial translation and axial rotation.

The intramedullary nail is, preferably, roughly circular in cross section and elongated although any number of cross sectional shapes may be used. The nail is, preferably, cannulated and anatomically curved to fit the shape of a bone.

The cannulated intramedullary nail allows passage of one or more anchoring tang assemblies. These anchoring tang assemblies are inserted from the proximal end and telescoped through the axial bore towards the distal end by a insertion/deployment/retraction instrument. An alternate embodiment has a retracted tang mounted on a tang assembly that is permanently placed within the intramedullary nail and is deployed and retracted by the above mentioned instrument.

The proximal end of the nail contains a securing arrangement for a tool for driving and extracting the nail. The tool advantageously cooperates with a slot in the proximal end of the nail so that the desired angular disposition of the nail is indicated and easily maintained during insertion of the nail.

When the intramedullary nail is placed into position, the anchoring tang assembly is actuated to deploy the tangs outwardly from their stowed position through the portals and into the cortical bone. The interlocking of the intramedullary nail to the cortical shell of the long bone may be achieved, at least once, using at least one screw or at least one tang assembly. In the preferred embodiment, several tang assemblies would be positioned longitudinally within the nail based on the fracture location and the surgeon's assessment for proper fixation. The tangs are deployed to any desired position thereby achieving a desired fixation and rotation prevention based upon the quality of the bone. Should the system require additional load carrying capability, cortical screws may be placed to further secure the nail with the surrounding bone.

The anchoring tang assembly contains arcuate shaped tangs that are permanently attached to the tang assembly body. These tangs are initially formed into a prescribed position for storage. As the assembly is actuated, the tangs deploy and are formed into their final shape through interaction with the portal in the nail.

The end cap preferably contains a coating of ultra-high molecular weight polyethylene (UHMWPE) within the threads. This provides constant positive engagement between the end cap external threads and the intramedullary nail internal threads preventing loosening of the end cap due to bodily forces.

Should the situation arise in which the surgeon requires removal of the intramedullary system, the tangs are completely reversible. The end cap is removed and the tang assembly insertion/deployment/retraction instrument is inserted through the axial bore. When the first tang assembly is encountered, a force is exerted on the instrument against the tang body causing the body to move longitudinally resulting in the tangs engaging the portal and pulling away from the bone and returning inside the nail. Once the tangs are completely inside the axial bore, the tang assembly is free to slide within the intramedullary nail. Force is continually applied, to the instrument, telescoping the instrument and tang assembly further along the nail until another tang assembly is encountered. The first tang assembly will "nest" with the second tang assembly. Upon continued pressure, the entire assemblage telescopes through the axial bore until the last tang assembly has been retracted and rests against the bottom of the axial bore of the intramedullary nail. The nail can then be extracted from the bone.

In one embodiment of the present invention, the intramedullary nail system is combined into a kit which includes several intramedullary nails of differing lengths and/or diameters and/or shapes, each having an axial bore, radial bores and portals which allow passage of different sized locking screws and anchoring tangs through the nails into the surrounding bone. The intramedullary nails have a distal end and a proximal end with internal threads in the proximal end. Several like-sized end caps are provided in the kit, each with external threads to cooperate with the internal threads in the proximal ends of the nails. Different sized tang assemblies are in the kit for selective telescoping movement through like-sized axial bores of the several nails. The tang assemblies may differ in diameter and/or in the length of the tangs carried by the tang assemblies. Also in the kit are several different sized cortical screws for use in conjunction with the nails. One or more insertion/deployment/retraction instruments are provided in the kit to manipulate the tang assemblies in the axial bore of a nail to deploy the tangs through the portals into a bone. The instrument is of a length that it may be manipulated at the proximal end of the nail to deploy or retract tangs at the distal end of the nail. The kit allows the surgeon flexibility in selecting the proper nail system for the fracture presented by the patient. The entire kit may be sterilized and presented in the operating room or some choices may be made earlier as to the elements to be used in a particular situation.

Finally, once the intramedullary nail is locked into the bone a condition known as stress shielding is typically inherent in the bone. As the bone heals these stresses need to be relieved. The bone can heal in a pre-stressed condition and refracture at a later date or the nail rotates with respect to the bone and repeated loading causes screw failure.

Clearly a need exists for a system that offers the ease of insertion and superior performance of existing intramedullary nails while minimizing the surgical insult to the human body and eliminates the need for distal screw targeting. Such a system would include a simple, effective and controllable fixation device which allows greater purchase of the bony fragments, provides a means of rotational stability in the femoral shaft, and offers to minimize, if not eliminate the need for additional distal incisions to locate and place locking screws. This system would be designed to allow the surgeon a choice of penetration distance within the femoral shaft and fixation based upon the injuries presented and the desired level of treatment. Finally, this system would allow explantation to occur as easily as implantation.

BRIEF DESCRIPTION OF THE DRAWINGS

FIG. 1 is a perspective view, partially in cross section, of the intramedullary system placed in a bone;

FIG. 2 is a perspective view, in partial longitudinal cross section, showing cortical screws;

FIG. 4A is a longitudinal cross section of the nail showing the nested tang assemblies;

FIG. 4B is an enlarged partial cross section of FIG. 4A;

DETAILED DESCRIPTION

The individual components of the assembly, as illustrated in FIG. 1 and FIG. 2, are constructed of implantable grade stainless steel alloys in the preferred embodiment but could also be constructed of implantable grade titanium alloys as well. These components consist of the nail body 1, the tang assembly 2, the end cap 3, and the optional cortical screws 4.

Figure 3B:
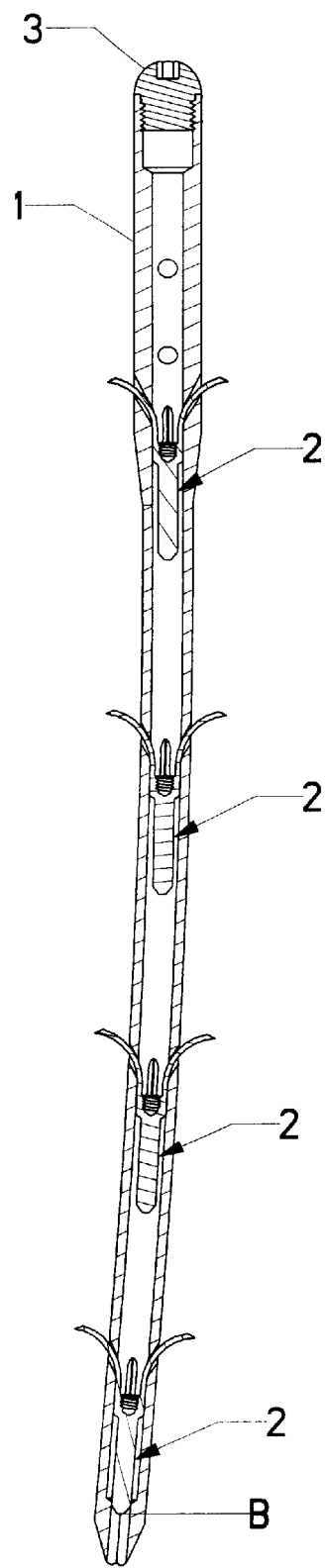
FIG. 3B is a longitudinal cross section of the nail shown in FIG. 3A.
Figure 3A:
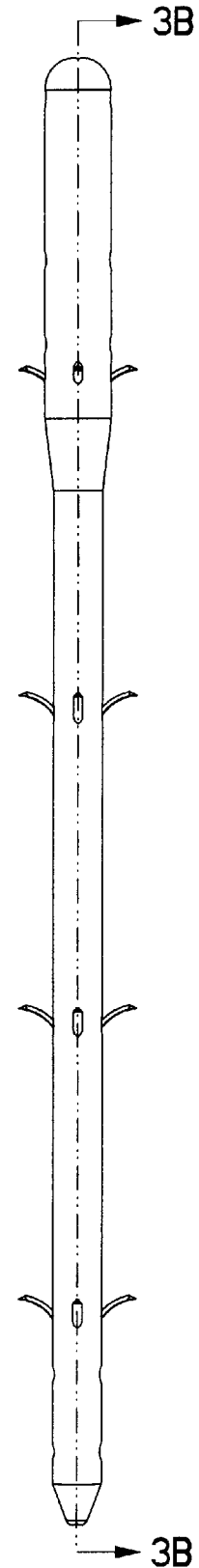
FIG. 3A is a perspective of the intramedullary nail and tang assembly of FIG. 1.
Figure 5A:
FIG. 5A is a side perspective of the intramedullary nail.
Figure 5B:
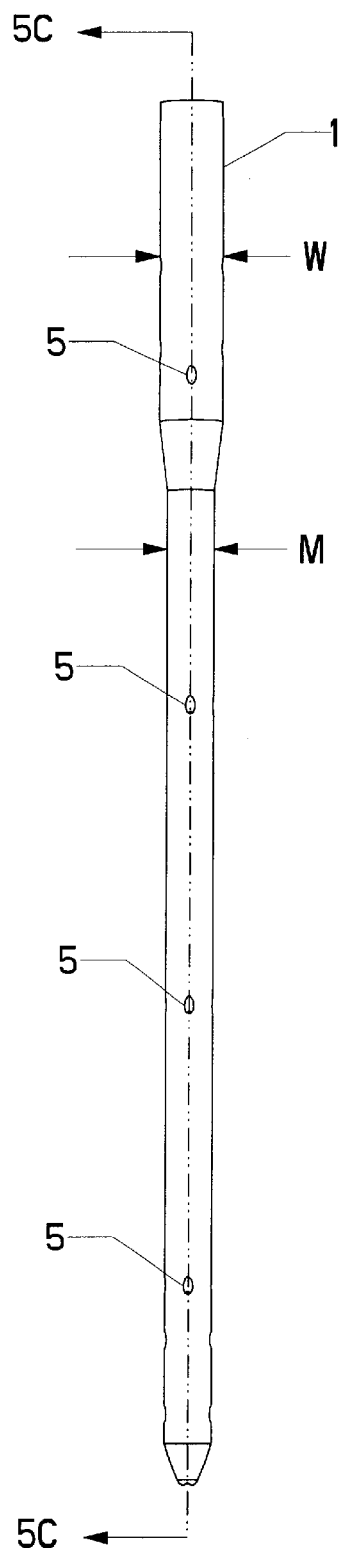
FIG. 5B is a front perspective of FIG. 5A.
Figure 5C:
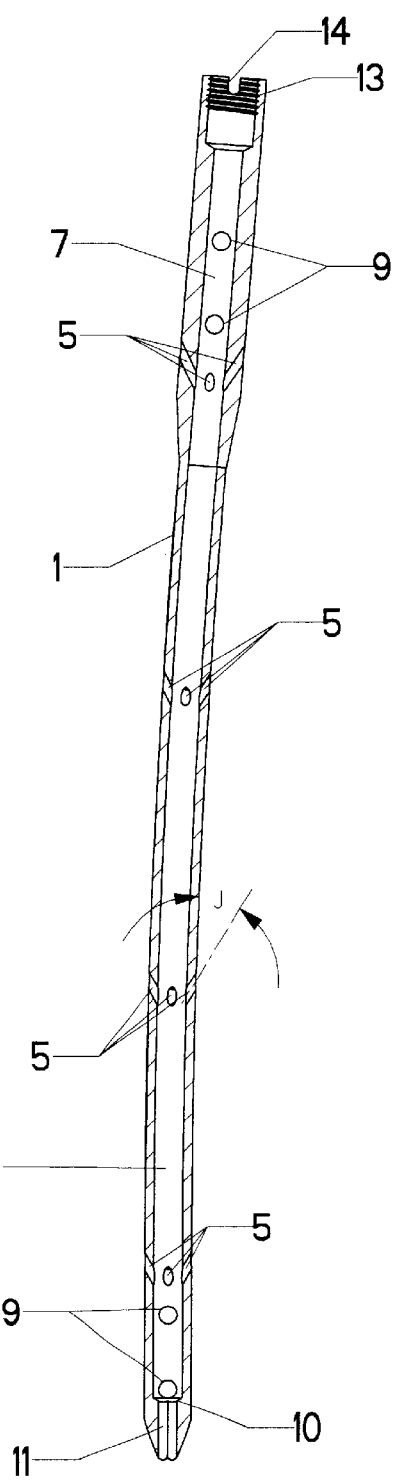
FIG. 5C is a longitudinal cross section along line 5C—5C of FIG. 5B.

The nail body, of FIGS. 5 A, B, C, is anatomically designed for antegrade insertion into the intramedullary canal of a long bone. However, retrograde insertion into the intramedullary canal is possible with a nail body of similar function, but different anatomical shape. The proximal outside diameter W of the nail body 1 is greater than the distal outside diameter M to improve the fit within the proximal bone. Applications within other long bones may result in the proximal outside diameter W being equal to the distal outside diameter M. Along the length of the nail body 1 are multiple sets of four tang portals 5, as shown in FIGS. 3A and 3B. A lesser or greater number of circumferential tangs and portals may be employed with the intramedullary nail system (not shown). Each set of four tang portals 5 are located on a 90 degree radial spacing penetrating from the leading outside diameter M into the distal bore 6, on axes which form an angle J to the distal outside diameter M. This angle J is critical to the proper formation and exit of the tang 16. The clearance holes 9 of FIG. 5C pass through the distal outside surface and wall into the distal bore 6 and continue on the same axis through the opposite wall and outer diameter. Their diameter is such as to allow passage of the threaded portion of the cortical screw 4 shown in FIG. 2. A frusto-conical surface 10 (FIG. 5C) provides a transition between the circular bore 6 and the bore 11. The bore 11 serves three purposes: It provides clearance through the leading end of the nail body 1 for passage of a guide pin, used during fracture alignment and installation of the nail body 1 into the intramedullary canal, it provides a sliding fit for the forward protrusion 18 (FIG. 6A) of tang assembly 2, and it acts as a "vent" hole for any organic material within the bore 6 which is being pushed ahead of the tang assembly 2 during tang assembly 2 installation. It must be noted that the forward most clearance holes 9 also intersect the frusto-conical feature 10 and will act as vents for organic material during tang assembly 2 insertion after the protrusion 18 has engaged and filled bore 11. The internal threads 13 at the trailing end of the nail body 1 provide for instrument interface, as do slots 14. The threads 13 are used for attachment and the slots 14 for radial alignment. The internal threads 13 also engage the external threads 23 shown in FIG. 7A of end cap 3.

Figure 6A:
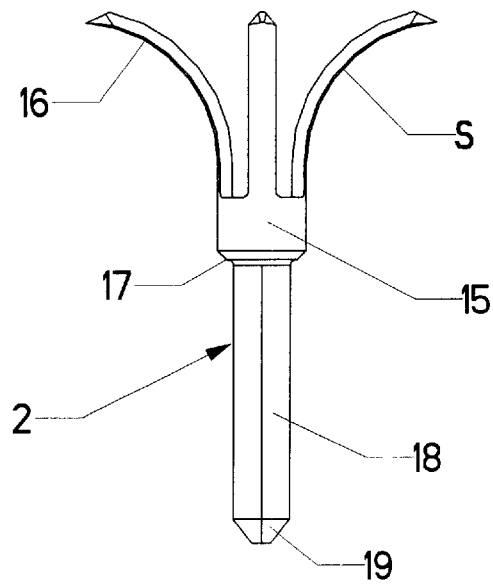
FIG. 6A is an enlargement of a deployed tang assembly of FIG. 3A.
Figure 6C:
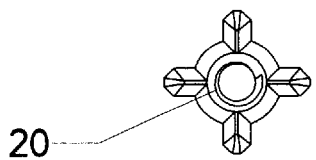
FIG. 6C is a top view of FIG. 6B.
Figure 6B:
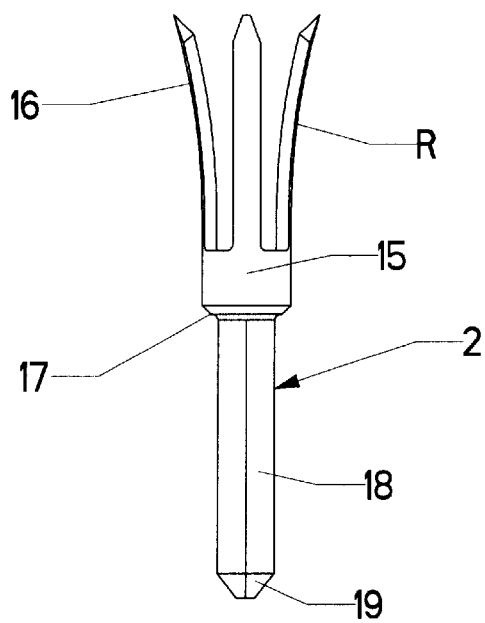
FIG. 6B is an enlargement of tang assembly of FIG. 6A in the stowed state.
Figure 7A:
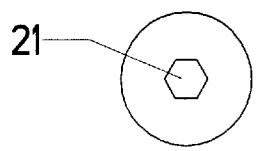
FIG. 7A is a top view of the end cap of FIG. 3A.

The tang assembly 2 has four equally sized and radially spaced tangs 16 which are preformed to radius R. The radius R (FIG. 6B) on each tang 16 results in a dimension between the trailing ends of opposing legs which is greater than the outside diameter of tang body 15 and the bore diameter 6 of nail body 1. The tang body 15 is circular in cross section and sized for a sliding fit within nail body bore 6 with a leading edge chamfer 17 which transitions into the leading protrusion 18 which has a square cross section and leading end taper 19. Tang body 15 contains an internally threaded bore 20 which is the instrument interface for the insertion/deployment/retraction instrument 25 used to insert and deploy the tang 16 of tang assembly 2. It must be noted that threaded bore 20 is not needed for tang retraction. FIG. 6A illustrates the deployed shape of tang assembly 2 which is the shape it assumes after the tangs have been forced through the tang portals 5 of nail body 1.

Insertion/deployment of the tang assemblies 2 occurs after insertion of the nail body into the intramedullary canal. The insertion/deployment instrument is threaded into the threaded bore 20 of the most distal tang assembly 2. The most distal tang assembly 2 is now inserted through nail body proximal bore 7 and into nail body distal bore 6. Since the distance between opposing tangs 16 is greater than the bore diameter 6 due to radius R, the interference with bore 6 forces the tangs 16 inward in an elastic manner and insertion continues. As the tang travels down bore 6, any organic material which has accumulated in bore 6 is pushed ahead and forced out through bore 11 of nail body 1 and through clearance holes 9. Further insertion causes the tang assembly 2 leading taper 19 to contact the bore 11 of the nail body 1. Since both cross sections are matched, no engagement will occur until they are radially aligned which may or may not occur without some slight rotation of the tang assembly 2 using the insertion/deployment instrument. After alignment occurs and by virtue of this alignment, the tang leading protrusion 18 will slide freely in bore 11 and the tangs 16 and the nail body 1 tang portals 5 will now be aligned. The tang assembly 2 continues past tang portals 5 and is fully inserted when the tang body leading edge chamfer 17 makes contact with the nail body frusto-conical feature 10 at point C FIG. 4B. In this position, the leading end of tang assembly 2 protrudes through the end of nail body 1 to point A and the trailing end of the tangs 16 are just past tang portals 5. The tang is now in position to be deployed. To deploy the tang, an axial force is exerted by the insertion/deployment instrument in the opposite direction as for insertion. This causes the tang assembly 2 to translate back up bore 6 and the sharp ends of tangs 16 to encounter tang portals 5. Since the tangs 16 were resiliently compressed inward by bore 6 they will now spring outward forcing the sharp end of tangs 16 into tang portals 5. Further translation of the tang assembly 2 forces the tangs 16 through the tang portals 5. Due to the diameter and angle of the tang portals 5, the tangs 16 are formed in such a manner as to emerge almost perpendicular to the femoral cortex at a final radius S. Continued translation of the tang assembly 2 causes the tangs 16 to penetrate the femoral cortex. During this time, tang leading protrusion 18 is still engaged by the nail body bore 11 thus preventing rotation of tang assembly 2 in bore 6 during deployment and preventing unwanted twisting of the tangs 16. The tang assembly 2 can be deployed fully or partially and is self locking in any position due to the almost perpendicular entry angle into the cortex. After deployment, the insertion/deployment instrument is unthreaded from tang threaded bore 20 and removed. The nail body 1 is now fixed axially and rotationally in the intramedullary canal. FIG. 3B shows the tang assembly 2 in the fully deployed position having translated a distance from point A FIG. 4B to point B FIG. 3B. The tangs 16 are fully retractable. Tangs 16 are retracted by applying a force on the tang assembly 2 with instrumentation in the opposite direction as deployment until the tang assembly 2 comes to rest at points C and A FIG. 4B.

Placement of additional tang assemblies 2 and deployment of tangs 16 is accomplished in much the same manner as that described above. As the more proximal tang assemblies 2 are added the insertion/deployment instrument 25 plays a more important role in obtaining proper alignment with the respective tang portals 5. FIG. 1, 3A and 3B show deployment of multiple tang assemblies 2.

Distal fixation of the nail body 1 can be accomplished without use of tang assembly 2. This is accomplished by using the cortical screws 4 (FIG. 2). The cortical screws 4 are placed through the lateral femoral cortex and through clearance holes 9 in the nail body 1, then through the medial femoral cortex FIG. 2. The cortical screws are not used in conjunction with distal tang fixation and cannot be passed through clearance holes 9 if there is a tang assembly 2 inserted into nail body 1 at that location.

Figure 7B:
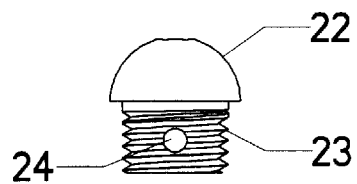
FIG. 7B is a perspective of the end cap of FIG. 7A.

The end cap 3 is inserted into the proximal end of nail body 1 until external threads 23 (FIG. 7B) contact the internal threads 13 of nail body 1. The end cap 3 is then rotated clockwise by means of hexagonal recess 21 to engage the threads. End cap 3 contains a coating of ultra high molecular weight polyethylene (UHMWP) 24 which acts as a thread locking element to help prevent unwanted loosening of end cap 3. The top surface 22 of end cap 3 is rounded to provide an anatomic fit with the surrounding bone, thus eliminating irritation against the surrounding musculature.

We claim:

1. An intramedullary nail for reducing and stabilizing fractures in long bones comprising an elongated body sized and shaped for insertion in the intramedullary canal of said bone, said elongated body having a proximal end and a distal end, said proximal end to be disposed on one side of a fracture and said distal end to be disposed on the other side of a fracture, said elongated body having an axial bore throughout the length, said proximal end having a plurality of radial bores extending through said axial bore and said elongated body normal to said axial bore, said distal end having a plurality of radial bores extending through said axial bore and said elongated body normal to said axial bore, said proximal end having at least one portal extending through said elongated body from said axial bore, said distal end having at least one portal extending through said elongated body from said axial bore, a tang assembly disposed in said axial bore for longitudinal movement therein, said tang assembly including a resilient tang for radial deployment, said tang resiliently extending through one of said portals upon longitudinal movement of said tang assembly wherein at least one cortical screw is adapted to be inserted through said bone and one of said plurality of radial bores to provide additional load carrying capability.

2. An intramedullary nail of claim 1 wherein said tang is arcuate in shape upon radial deployment to apply compression between said proximal end and said distal end of said elongated body.

3. An intramedullary nail of claim 2 wherein an end cap is removably connected to said proximal end of said elongated body.

4. An intramedullary nail of claim 1 wherein has a reduced cross section, said tang assembly having a leading end and a trailing end, the shape of said leading end corresponding to said reduced cross section preventing rotational movement of said tang assembly during longitudinal movement.

5. An intramedullary nail of claim 4 wherein a retraction instrument is telescoped through said axial bore of said elongated body, said retraction instrument having a leading end and a trailing end, said leading end of said instrument temporarily engaging said trailing end of said tang assembly, said trailing end of said instrument extending outwardly from said proximal end whereby manipulation of said trailing end of said instrument causes longitudinal movement of said tang assembly and deployment of said tang.

6. An intramedullary nail of claim 5 wherein said manipulation of said trailing end of said instrument is rotational.

7. An intramedullary nail of claim 5 wherein said manipulation of said trailing end of said instrument is longitudinal.

8. An intramedullary nail of claim 1 wherein said distal end has a plurality of portals, said proximal end has a plurality of portals, a plurality of tang assemblies disposed in said axial bore at the distal end corresponding to said plurality of portals in said distal end, a plurality of tang assemblies disposed in said axial bore at said proximal end corresponding to said plurality of portals in said proximal end, said tangs of each of said tang assemblies extending through said corresponding portals of said distal end and said proximal end.

9. An intramedullary nail of claim 8 wherein at least one tang assembly is disposed in said axial bore at said distal end and at least one tang assembly is disposed in said axial bore at said proximal end, said tang of said tang assembly disposed in said axial bore at said distal end extending through a portal of said plurality of portals in said distal end and said tang of said tang assembly disposed in said axial bore at said proximal end extending through a portal of said plurality of portals in said proximal end whereby said tangs may be selectively deployed along said elongated body.

10. An intramedullary nail kit for fixing bone fractures comprising a plurality of different sized elongated bodies shaped for insertion in the intramedullary canal of a long bone, each elongated body having a proximal end for disposition on one side of a fracture, a distal end for disposition on the other side of a fracture and an intermediate portion connecting said proximal and distal ends, said elongated body having an axial bore throughout;

a plurality of end caps adapted for insertion in said axial bores in said proximal end of said different sized elongated bodies;

each end cap and said proximal end having cooperating structure for removably securing said end cap to said elongated body;

said proximal ends of said different sized elongated bodies having at least one radial bore extending through said axial bores and normal thereto;

said distal ends of said different sized elongated bodies having at least one radial bore extending through said axial bore and normal thereto;

at least one portal in said proximal ends of said different sized elongated bodies;

at least one portal in said distal ends of said different sized elongated bodies; and at least one portal in said intermediate portions of said different sized elongated bodies;

said portals each including at least one bore extending from said axial bore at an obtuse angle;

a plurality of tang assemblies adapted to slidably traverse said axial bores of said different sized elongated bodies, each of said plurality of tang assemblies having at least one resilient tang, some of said tang assemblies having a different sized resilient tang, each of said resilient tangs adapted to be deployed through one of said portals into a bone;

a plurality of different sized cortical bone screws adapted to traverse a bone and said radial bores in said distal end and said proximal end of said plurality of different sized elongated bodies; and an instrument for movably engaging one of said plurality of tang assemblies;

said instrument adapted to slide said tang assembly through said axial bore and manipulate said tang assembly to deploy said tang;

whereby a particular sized intramedullary nail having particular sized tangs may be selected from said kit to fix a fracture in different sized bones, said instrument slides at least one particular sized tang assembly through said axial bore and manipulates said tang assembly to deploy said particular sized tang into the bone, said instrument is removed from said axial bore and one of said end caps is removaby secured in said axial bore at said proximal end to close said axial bore.

11. An intramedullary nail kit of claim 10 wherein said tang assemblies have at least two tangs on opposite sides of said tang assembly and said portals have at least two obtuse bores on opposite sides of said axial bore.

12. A method of reducing and fixing fractures in long bones comprising the steps of a) providing an intramedullary nail having an elongated body with an axial bore, said elongated body having a proximal end and a distal end, said proximal end having a plurality of radial bores extending through said axial bore and said elongated body normal to said axial bore, said distal end having a plurality of radial bores extending through said axial bore and said elongated body normal to said axial bore, said proximal end having a plurality of portals in said elongated body, said distal end having a plurality of portals in said elongated body, each of said portals comprised of a plurality of circumferential bores through said elongated body, b) inserting said intramedullary nail into the intramedullary canal of a fractured long bone with said proximal end disposed on one side of said fracture and said distal end on the other side of said fracture, c) providing a retraction instrument having a size and shape to be telescoped through said elongated body, said instrument having a leading end adapted to be disposed adjacent said distal end and a trailing end adapted to be disposed adjacent said proximal end, said leading end including deployment structure, d) providing a tang assembly having a tang body with cooperating structure for engaging said deployment structure and a plurality of tangs disposed about the circumference of said body, said tangs sized and shaped to extend through said circumferential bores of said portals, e) inserting a tang assembly in said axial bore at said proximal end and longitudinally displacing said assembly toward said distal end of said elongated body with said retraction instrument, f) manipulating said trailing end of said retraction instrument to engage said deployment structure and said cooperating structure to extend said tangs through said circumferential bores into said bone securing said distal end about said radial and said axial axes, g) disengaging and removing said retraction instrument, h) repeating steps e)–g) to insert a plurality of tang assemblies including inserting tang assemblies in said proximal end of said elongated body, i) providing an end cap sized and shaped to close the axial bore in said proximal end of said elongated body and securing said end cap in said axial bore.

13. A method of claim 12 including the step of inserting a cortical screw through said bone and through one of said plurality of radial bores.

14. A method of claim 12 including removing said tangs from said bone by unsecuring said end cap from said axial bore of said proximal end, removing said end cap, inserting said retraction instrument in said axial bore, engaging a tang assembly and longitudinally displacing a first said tang assembly toward said distal end of said elongated body thereby causing said first tangs to retract into said axial bore, further longitudinally displacing said first tang assembly to contact a second said tang assembly, further longitudinally displacing said first and second tang assemblies to cause said tangs of said second tang assembly to retract into said axial bore and continuing said longitudinal movement toward said distal end until all tangs are retracted into said axial bore.

* * * * *